United States Patent
Sandoz

(10) Patent No.: US 7,640,817 B2
(45) Date of Patent: Jan. 5, 2010

(54) METHOD FOR DETERMINING THE STATE OF A WOODEN SUPPORT

(76) Inventor: Jean-Luc Sandoz, Chemin de la Brume 4, Appt. 76, Morges (CH) CH-1110

( * ) Notice: Subject to any disclaimer, the term of this patent is extended or adjusted under 35 U.S.C. 154(b) by 460 days.

(21) Appl. No.: 11/577,362

(22) PCT Filed: Oct. 17, 2005

(86) PCT No.: PCT/FR2005/050859

§ 371 (c)(1), (2), (4) Date: Apr. 17, 2007

(87) PCT Pub. No.: WO2006/042996

PCT Pub. Date: Apr. 27, 2006

(65) Prior Publication Data

US 2008/0028836 A1     Feb. 7, 2008

(30) Foreign Application Priority Data

Oct. 20, 2004   (FR)  .................... 04 52375

(51) Int. Cl.
*G01N 33/00*     (2006.01)
(52) U.S. Cl. ......................................... 73/866; 248/511
(58) Field of Classification Search .................... 73/866
See application file for complete search history.

(56) References Cited

U.S. PATENT DOCUMENTS

| | | | |
|---|---|---|---|
| 4,926,691 A | 5/1990 | Franklin | |
| 5,094,890 A * | 3/1992 | Smith et al. | 427/393 |
| 5,731,096 A * | 3/1998 | Besner et al. | 428/514 |
| 6,753,016 B2 * | 6/2004 | Ghosh | 424/604 |
| 7,008,997 B2 * | 3/2006 | Kovacs | 524/770 |

FOREIGN PATENT DOCUMENTS

| | | |
|---|---|---|
| EP | 0 634 655 | 1/1995 |
| FR | 2 758 883 | 7/1998 |
| FR | 2 816 710 | 5/2002 |

OTHER PUBLICATIONS

Sandoz J.L. et al. "Wood poles ageing and non destructive testing tool" Cired 97. Proceedings of the 14th International Conference and Exhibition on Electricity Distribution, IEE, London, UK, vol. 3, No. 438, 2 juin 1997, pp. 26.1-26.6.

Ezer E. "Measurement of Wood Pole Strength—Polux (R) a New Non-Destructive Inspection Method" 2001 Rural Electric Power Conference, Little Rock, AR, USA, Apr. 29-May 1, 2001; IEEE, NY,NY,USA Apr. 29, 2001, pp. C6/1-7.

Nelson R.F. "Reliability-Centered Power Line Management—Inspection Process, Measurement Techniques and Data Management Considerations", IEEE Colloquium on Distribution Overhead Lines—Economics, Practice and Technology of Reliability Assessment, IEE< London, US No. 1998/289, May 19, 1998, p. 3/1-24.

* cited by examiner

*Primary Examiner*—Hezron Williams
*Assistant Examiner*—Rodney T Frank
(74) *Attorney, Agent, or Firm*—Heslin Rothenberg Farley & Mesiti P.C.

(57) ABSTRACT

A method for determining the state of preservation of a wooden support and establishing a diagnosis in order to find out whether the wooden support is in a state which is suitable for use, in a state requiring a maintenance operation or in a state requiring its elimination includes measuring the hardness of the wooden support and the hygrometricity of the wooden support. The method further includes determining the species of the timber of the wooden support, determining the treatment previously applied to the wooden support, calculating the resulting safety residual stress, comparing the value of the calculated safety residual stress with an observed average safety residual stress and establishing a diagnosis depending on this comparison.

5 Claims, No Drawings

METHOD FOR DETERMINING THE STATE OF A WOODEN SUPPORT

CROSS-REFERENCE TO RELATED APPLICATIONS

This application is a Section 371 filing of International Application No. PCT/FR2005/050859 filed on Oct. 17, 2004 and published, in French, as International Publication No. WO2006/042996 on Apr. 27, 2006, which claims priority of French Application No. 0452375 filed on Oct. 20, 2004, which applications are hereby incorporated by reference herein, in their entirety.

BACKGROUND ART

The present invention relates to a method for determining the physical and sanitary state and establishing a diagnosis of a wooden support such as a wooden telephone pole or electricity pole or any other wood-based structure with a round or other cross-section.

Millions of wooden utility poles are in use and are periodically inspected in order to ensure maintenance of such lines. Despite chemical pre-treatment, these wooden poles gradually deteriorate due to atmospheric action and fungal attack. One of the main problems encountered with such wooden supports is inspecting them periodically in order to check their condition in order to decide whether they are suitable for use, require maintenance or need replacing.

DESCRIPTION OF THE PRIOR ART

Document EP-634.655 discloses a device making it possible to inspect the physical state of a wooden support simply, effectively and quickly. This device makes it possible to measure hardness and hygrometricity simultaneously.

However, this device does not take into account other important parameters such as the type of timber or its treatment which may cause changes and variations in the measured hardness and hygrometricity. In addition, using the two measured variables, the interpretation of values is complex and can even result in erroneous results.

FIELD OF THE INVENTION

The main problem which the invention aims to solve is to develop a simple, fast method for determining the state of a wooden support. The second problem is to devise a method that makes it possible to include new parameters specific to the support in order to improve the reliability of the diagnostic results obtained. The third problem is to implement a method for diagnosing the state of a wooden support on the basis of two measurable parameters—the hardness and the hygrometricity of the wooden support.

As is known, a method for determining the state of preservation of a wooden support and establishing a diagnosis in order to find out whether the wooden support is in a state which is suitable for use, in a state requiring a maintenance operation or in a state requiring its elimination, consisting of measuring:

the hardness (F) of the wooden support, and
the hygrometricity (H) of the wooden support.

According to a first aspect of the invention, the method is characterised in that it also comprises the following steps:

determining the timber species of the wooden support;
determining the treatment previously applied to the wooden support;
calculating the resulting safety residual stress ($\sigma$) using the formula:

$$\sigma = \alpha . F - \beta . H + \epsilon$$

where $\alpha$, $\beta$, and $\epsilon$ are calibration coefficients that depend on the timber species and the treatment previously applied to the wooden support; and comparing the value of the calculated safety residual stress ($\sigma$) with an observed average safety residual stress;
establishing the diagnosis based on this comparison.

In other words, by including new parameters (timber type and the treatment applied to the timber), the calculation performed by determining the residual stress will improve the diagnoses for inspected timbers. Moreover, correlating the strength of the timber with the moisture content of the timber in order to calculate the residual stress will facilitate and speed up determination of the state of the timber and produce an accurate diagnostic result.

A diagnosis of this type therefore ensures the reliability of the wooden supports as well as improved maintenance management. All the actual data is measured and stored. Comparison is performed by a programmable machine which converts the signals into displays for the user by using LEDs to indicate various states, for instance "very good condition", "good condition", "weakening or weakened" and "severely weakened and hazardous".

In a first embodiment, if the treatment previously applied to the wooden support is based on metallic salts, $\alpha > 0$, $\beta \geq 0$ and $\epsilon < 0$ can be used as calibration coefficients. In a second embodiment, if the treatment previously applied to the wooden support is based on phenolic compounds, $\alpha > 0$, $\beta > 0$ and $\epsilon > 0$ can be used as calibration coefficients.

In an especially advantageous manner, the method may also comprise the following steps:

measuring the natural frequency of the wooden support which will depend on the state of preservation and the ratio $(D/L)^3$, where D is the diameter of the wooden support and L is the length of the wooden support; and
calculating the stress ($\sigma_z$) associated with the natural frequency of the pole using the formula:

$$\sigma_z = f(D^3/L^3)$$

where $f$ is a function that associates the stress of the pole to its natural frequency.

The method may preferably also comprise the following steps:

calculating the residual stress ($\sigma_{res}$) using the formula:

$$\sigma_{res} = \sigma_s + \sigma_z + \zeta$$

where $\sigma_s$ is the calculated safety residual stress, $\sigma_z$ is the stress associated with the pole's natural frequency and $\zeta$ is a calibration coefficient that depends on the species of the timber and the treatment previously applied to the wooden support;

comparing the value of the calculated safety residual stress ($\sigma_{res}$) with an average safety residual stress observed or laid down by a standard and;
establishing the diagnosis based on this comparison.

The invention and its various advantages and different characteristics will be more readily understandable from the following description given merely by way of example.

DESCRIPTION OF THE PREFERRED EMBODIMENTS

The species used for wooden supports are as follows: pine, fir, larch, spruce, cedar, chestnut and eucalyptus in southern hemisphere regions.

The most widely used treatments for wooden supports are:
based on metallic salts such as chrome, copper, arsenic (CCA) or copper, chrome and boron (CCB);
or based on phenolic compounds of the pentachlorophenol or creosote type.

The device described in Document EP-634.655 measures the force (F) expressed in daN, the humidity (H) expressed in % after the spikes of the device have penetrated into the timber by 40 mm for poles having a diameter of 10 cm to 35 cm or more.

The safety residual stress resulting from F and H, expressed in $N/mm^2$, is calculated using the formula: $\sigma = \alpha.F - \beta.H + \epsilon$ In the following Tables, in terms of safety, "Good σ" is equivalent to a "Very good condition" diagnosis, "Average σ" is equivalent to a "Good condition" diagnosis, "Mediocre σ" is equivalent to a "Weakening and weakened" diagnosis and "Poor σ" is equivalent to a "Severely weakened and hazardous" diagnosis.

In the following Tables, in terms of maintenance operations, "Good σ" is equivalent to a "Very good condition" diagnosis, "Average σ" is equivalent to a "Needs monitoring" diagnosis, "Mediocre σ" is equivalent to a "Needs replacing" diagnosis and "Poor σ" is equivalent to a "Severely weakened and hazardous" diagnosis.

In order to supplement these measurements, a third physical parameter may be included in order to take into account damage below ground level—natural frequency. This frequency is a function of the ratio: $\sigma_z = f(D^3/L^3)$, where D is the diameter of the pole at ground level and L is its length.

The natural frequency falls very quickly if the buried length has deteriorated.

In fact, a utility pole that has deteriorated significantly 20 cm or 30 cm below ground level cannot be detected by the test nor by any other non-destructive test method. By exciting the pole manually, for instance by banging it with the hand or by striking it with a hammer, one can cause it to resonate and one can use a chronometer or even an accelerometer or equivalent system to measure its natural frequency.

A natural-frequency test is therefore added to the basic model if damage to the foundation is suspected.

Results

For France, the calibration coefficient values $\alpha$, $\beta$, and $\epsilon$ are as follows:

| Treatment | α | β | ε |
|---|---|---|---|
| Creosote | 0.3 | 0.1 | 7.4 |
| CCA salts | 0.225 | 0 | −0.613 |

As far as safety is concerned, calculating the resulting safety residual stress values (σ) gives the following results:

| Treatment | Poor σ | Mediocre σ | Average σ | Good σ |
|---|---|---|---|---|
| Creosote | <18.3 | 18.3-23 | 23-28 | >28 |
| CCA salts | <18.3 | 18.3-23 | 23-28 | >28 |

As far as maintenance operations are concerned, calculating the average maintenance safety residual stress values (σ) gives the following results:

| Treatment | H(%) | Poor σ | Mediocre σ | Average σ | Good σ |
|---|---|---|---|---|---|
| Creosote | >120 | <22 | >22 | — | — |
|  | 50-120 | <18.3 | 18.3-22 | >22 | — |
|  | <50 | <18.3 | 18.3-22 | 22-26 | >26 |
| CCA salts | >130 | <22 | >22 | — | — |
|  | 60-130 | <18.3 | 18.3-22 | >22 | — |
|  | <60 | <18.3 | 18.3-22 | 22-26 | >26 |

For Germany, the calibration coefficient values $\alpha$, $\beta$, and $\epsilon$ are as follows:

| Treatment | α | β | ε |
|---|---|---|---|
| Creosote | 0.4 | 0.1 | 7.4 |
| Salts | 0.225 | 0 | −0.613 |

For the United Kingdom, the calibration coefficient values $\alpha$, $\beta$, and $\epsilon$ are as follows:

| Treatment | α | β | ε |
|---|---|---|---|
| Creosote | 0.4 | 0.1 | 7.4 |
| Salts | 0.225 | 0 | −0.613 |

For Switzerland, the calibration coefficient values $\alpha$, $\beta$, and $\epsilon$ are as follows:

| Treatment | α | β | ε |
|---|---|---|---|
| CCB salts | 0.225 | 0 | −0.613 |

For Canada, the calibration coefficient values $\alpha$, $\beta$, and $\epsilon$ are as follows:

| Treatment | α | β | ε |
|---|---|---|---|
| Pentachlorophenol | 0.2 | 0.055 | 6.68 |

For Austria, using Austrian Standard ÖNORM E4200 (Overhead Power Lines; Wooden Poles), the values of calibration coefficients $\alpha$, $\beta$, and $\epsilon$ are as follows for larch:

| Treatment | α | β | ε |
|---|---|---|---|
| Creosote (80%) | 0.3 | 0.1 | 7.4 |
| CCA salts (20%) | 0.225 | 0.1 | −0.613 |

As far as safety is concerned, calculating the resulting safety residual stress values (σ) gives the following results:

| Treatment | Poor σ | Mediocre σ | Average σ | Good σ |
|---|---|---|---|---|
| Creosote | <22 | 22-30 | 30-40 | >40 |
| CCA salts | <18.3 | 18.3-23 | 23-28 | >28 |
| Concrete base (regardless of | <24 | 24-38 | 38-43 | >43 |

-continued

| Treatment | Poor σ | Mediocre σ | Average σ | Good σ |
|---|---|---|---|---|
| treatment) |  |  |  |  |
| Larch | <22 | 22-30 | 30-40 | >40 |
| (regardless of |  |  |  |  |
| treatment) |  |  |  |  |

As far as maintenance operations are concerned, calculating the average maintenance safety residual stress values (σ) gives the following results:

| Treatment | H(%) | Poor σ | Mediocre σ | Average σ | Good σ |
|---|---|---|---|---|---|
| Creosote | >90 | <30 | >30 | — | — |
|  | 40-90 | <22 | 22-30 | >30 | — |
|  | <40 | <22 | 22-30 | 30-40 | >40 |
| CCA salts | >130 | <22 | >22 | — | — |
|  | 60-130 | <18.3 | 18.3-22 | >22 | — |
|  | <60 | <18.3 | 18.3-22 | 22-26 | >26 |
| Concrete base | >50 | <38 | >38 | — | — |
| (regardless of | 25-50 | <23 | 23-38 | >38 | — |
| treatment) | <25 | <23 | 23-38 | 38-43 | >43 |
| Larch | >90 | <30 | >30 | — | — |
| (regardless of | 50-90 | <22 | 22-30 | >30 | — |
| treatment) | <50 | <22 | 22-30 | 30-40 | >40 |

The present invention is not confined to the embodiments described and illustrated. Numerous modifications can be made to this method after recalibration for new timber species and new timber treatments without thereby extending beyond the defined framework and scope of the claims.

The invention claimed is:

1. A method for determining the state of preservation of a wooden support and establishing a diagnosis in order to find out whether the wooden support is in a state which is suitable for use, in a state requiring a maintenance operation or in a state requiring elimination, comprising:

measuring hardness (F) of the wooden support;
measuring hygrometricity (H) of the wooden support;
determining timber species of the wooden support;
determining treatment previously applied to the wooden support;
calculating value of a resulting safety residual stress (σ) using the formula:

$$\sigma = \alpha.F - \beta.H + \epsilon$$

where α, β, and ε are calibration coefficients that depend on the timber species and the treatment previously applied to the wooden support; and
comparing the value of the calculated safety residual stress (σ) with an observed average safety residual stress; and
establishing the diagnosis based on said comparing.

2. A method as claimed in claim 1, wherein, if the treatment previously applied to the wooden support is based on metallic salts, $\alpha > 0$, $\beta \geq 0$ and $\epsilon < 0$ are used as the calibration coefficients.

3. A method as claimed in claim 1, wherein, if the treatment previously applied to the wooden support is based on phenolic compounds, $\alpha > 0$, $\beta > 0$ et $\epsilon > 0$ are used as the calibration coefficients.

4. A method as claimed in claim 1, further comprising:
measuring natural frequency of the wooden support which depends on state of preservation and ratio $(D/L)^3$, where D is diameter of the wooden support and L is length of the wooden support;
calculating stress ($\sigma_z$) associated with the natural frequency of the wooden support using the formula:

$$\sigma_z = f(D^3/L^3)$$

where $f$ is a function that associates stress of the wooden support to natural frequency of the wooden support.

5. A method as claimed in claim 4, further comprising:
calculating a value of residual stress ($\sigma_{res}$) using the formula:

$$\sigma_{res} = \sigma_s + \sigma_z + \zeta$$

where σs is the calculated value of safety residual stress, $\sigma_z$ is the stress associated with the pole's natural frequency and ζ is a calibration coefficient that depends on the species of the timber and the treatment previously applied to the wooden support;
comparing the value of the calculated safety residual stress ($\sigma_{res}$) with an average safety residual stress observed or laid down by a standard; and
establishing the diagnosis based on said comparing.

* * * * *